(12) United States Patent
Nair

(10) Patent No.: US 7,341,747 B2
(45) Date of Patent: Mar. 11, 2008

(54) CARRIER-FREE COMPOSITION FOR THE TREATMENT OF ONYCHOMYCOSIS

(75) Inventor: Muraleedharan G. Nair, Okemos, MI (US)

(73) Assignee: Board of Trustees of Michigan State University, East Lansing, MI (US)

( * ) Notice: Subject to any disclaimer, the term of this patent is extended or adjusted under 35 U.S.C. 154(b) by 407 days.

(21) Appl. No.: 10/949,681

(22) Filed: Sep. 24, 2004

(65) Prior Publication Data

US 2006/0068040 A1    Mar. 30, 2006

(51) Int. Cl.
*A61K 36/00* (2006.01)
*A61K 36/53* (2006.01)

(52) U.S. Cl. ...................... 424/725; 424/747

(58) Field of Classification Search ............ None
See application file for complete search history.

(56) References Cited

U.S. PATENT DOCUMENTS 6,344,190 B1    2/2002  Nair et al.
6,361,785 B1 *  3/2002  Nair et al. ................ 424/404

OTHER PUBLICATIONS

Calderone et al. J. Economic Entomol. 1995. vol. 88, No. 5, pp. 1211-1215.*
Nair, M.G. J. Natural Products. 1989. vol. 52, pp. 797-809.*
Skinner et al. J. Apicult. Res. 2001. vol. 40, No. 3-4, pp. 81-89.*
Nair, M.G., et al., J Nat Prod 52: 797-809 1989.

* cited by examiner

*Primary Examiner*—Christopher R. Tate
(74) *Attorney, Agent, or Firm*—Ian C. McLeod

(57) ABSTRACT

A composition for the treatment of onychomycosis (fungal nail disease) is described. The composition consists essentially of thymol, camphor, menthol and *Eucalyptus citridiora* as a colorless liquid oil without any carrier or solvent for these ingredients.

3 Claims, No Drawings

CARRIER-FREE COMPOSITION FOR THE TREATMENT OF ONYCHOMYCOSIS

CROSS-REFERENCE TO RELATED APPLICATIONS

Not Applicable

STATEMENT REGARDING FEDERALLY SPONSORED RESEARCH OR DEVELOPMENT

Not Applicable

STATEMENT REGARDING GOVERNMENT RIGHTS

Not Applicable

BACKGROUND OF THE INVENTION (1) Field of the Invention

The present invention relates to a carrier-free composition which is an onychomycosis (fungal nail disease) therapeutic agent. In particular, the present invention relates to a composition consisting essentially of thymol, camphor, menthol and *Eucalyptus citridiora* oil.

(2) Description of the Related Art

U.S. Pat. No. 6,344,190 to Nair et al describes the use of camphor, menthol, eucalyptus and thymol with a carrier which is a solvent for the ingredients; particularly, an ester of an alcohol such as isoamyl alcohol. This was done to solubilize the ingredients. It was thought that the carrier was necessary for this purpose.

OBJECTS

It is therefore an object of the present invention to provide a carrier-free composition wherein the ingredients are solubilized to provide a clear solution. It is further an object of the present invention to provide a method for the preparation of the composition. It is also an object of the present invention to provide a method for the use of the composition. These and other objects will become increasingly apparent by reference to the following description.

SUMMARY OF THE INVENTION

The present invention relates to a composition which consists essentially of (1) thymol, (2) camphor, (3) menthol and (4) *Eucalyptus citridiora* oil as ingredients in amounts which provide a colorless liquid in absence of a carrier. Preferably, the composition contains equal parts by weight of the ingredients. Further, the composition of the colorless liquid has been provided by a method which comprises stirring ingredients (1) to (3) into ingredient (4) to provide the colorless liquid. Still further, the composition of the ingredients (1) to (3) are introduced into ingredient (4) and then the mixture is heated to produce the colorless liquid. Preferably, the composition of the mixture has been heated up to about 80° C.

Further, the present invention relates to a method for the preparation of a pharmaceutical composition which comprises: mixing (1) thymol, (2) camphor, and (3) menthol into (4) *Eucalyptus citridiora* oil; and treating the mixture to provide a colorless oil. Preferably, the present invention relates to the method wherein the treating is by heating the mixture. Still further, the present invention relates to the method wherein the treating is by mixing the ingredients over a period of time to provide the colorless mixture.

Further still, the present invention relates to a method of treating toenail fungal infections which comprises: applying a composition which consists essentially of (1) thymol, (2) camphor, (3) menthol, and (4) *Eucalyptus citridiora* oil as ingredients in amounts which provide a colorless liquid in absence of a carrier. Preferably, the method of the composition contains equal parts of the ingredients.

The substance and advantages of the present invention will become increasingly apparent by reference to the following description.

DESCRIPTION OF THE PREFERRED EMBODIMENTS

Equal weights of thymol, camphor, menthol and *Eucalyptus citridiora* oil were used to formulate the TNF therapeutic agent resulting to a clear liquid that penetrates the cuticles and nails. The *Eucalyptus citridiora* oil was weighed first and stirred with equal weights of solid thymol, menthol and camphor. The mixture was then warmed to 80° C. till it forms a colorless liquid or stir at room temperature till the solids dissolve to form a colorless liquid. The resulting product is easy to apply on infected nails using a nail polish applicator or by a cotton swab.

Tests were performed with the composition on toenail fungi as follows:

Components in the formulation were equal weights of the following compounds 1-4:

1. Camphor

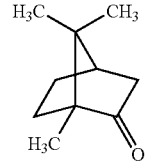

2. Menthol

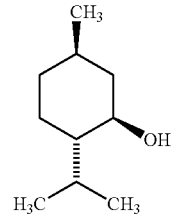

3. Thymol

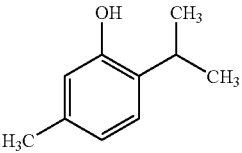

4. *E. citridiora* oil

Microbial cultures. All organisms, except the *Fusarium* and *Candida* spp., were purchased from American Type Culture Collection (ATCC), Manassas, Va., USA. The *Fusarium* and *Candida* spp. were Michigan State University (MSU) strains (Nair, M. G., Putnam, A. R., Mishra, S. K., Mulks, M. H., Taft, W. H., Keller, J. E., Miller, J. R., Zhu, P. P., Meinhart, J. D., Lynn, D. G. 1989. Faeriefungin: A new broad-spectrum antibiotic from *Streptomyces griseus* var. *autotrophicus. J Nat Prod* 52: 797-809).

Antimicrobial assay. *M. canis* (ATCC 42888), *E. floccosum* (ATCC 44685), *F. oxysporum* (MSU strain), *F. proliferatum* (MSU strain), *A. chrysogenum* (ATCC 22571), *A. strictum* (ATCC 46646), *A. terreus* (ATCC 52293), and *A. flavus* (ATCC 60040) were cultured in Petri dishes containing PDA medium (20 mL). *T. rubrum* (ATCC 28202), *T. mentagrophytes* (ATCC 42194), *S. brevicaulis* (ATCC 36139), and *S. dimidiatum* (ATCC 46921) were cultured in Petri dishes containing Emmon's modification of Sabouraud's agar medium (20 mL). *S. hyalinum* (ATCC 66093) was cultured in Petri dishes containing Malt extract agar medium (20 mL). The test organisms *C. albicans* (MSU strain), *C. kruseii* (MSU strain), and *C. parapsilosis* (MSU strain) were cultured in Petri dishes containing YMG media (20 mL).

The cells from a fully-grown plate of each organism were suspended in saline solution (5 mL) and diluted to obtain $5 \times 10^6$ CFU/mL using a hemacytometer. 50 μL of this suspension was used to inoculate 1 mL of respective growth medium of each test organism. Test formulation was added to the inoculated tubes at concentrations ranging from 250 to 5 μl/mL. The tubes containing cell cultures and compounds were incubated at 27° C. for 72-96 h. At the end of the incubation period, the tubes were examined for growth of the organism and further monitored for 7 days after which they were recorded for growth or no growth. The concentration at which no growth was observed or minimum concentration for 100% inhibition ($MIC_{100}$) is shown in Table 1 for each organism.

TABLE 1

$MIC_{100}$ (μg/mL) for the mixture containing equal weights of camphor, menthol, thymol and *Eucalyptus citriodora* oil against organisms causing onychomycosis.

| Organism | MIC |
| --- | --- |
| *Acremonium chrysogenum* | ≧20 |
| *A. strictum* | ≧20 |

TABLE 1-continued $MIC_{100}$ (μg/mL) for the mixture containing equal weights of camphor, menthol, thymol and *Eucalyptus citriodora* oil against organisms causing onychomycosis.

| Organism | MIC |
| --- | --- |
| *Aspergillus flavus* | ≧30 |
| *A. terreus* | ≧30 |
| *Candida albicans* | ≧50 |
| *C. kruseii* | ≧50 |
| *C. parapsilosis* | ≧50 |
| *Epidermophyton floccosum* | ≧30 |
| *Fusarium oxysporum* | ≧30 |
| *F. proliferatum* | ≧30 |
| *Microsporum canis* | ≧40 |
| *Scopulariopsis brevicaulis* | ≧30 |
| *Scytalidium dimidiatum* | ≧30 |
| *S. hyalinum* | ≧30 |
| *Trichophyton mentagrophytes* | ≧30 |
| *T. rubrum* | ≧30 |

The composition had a very broad spectrum of activity as can be seen from the results.

It is intended that the foregoing description be only illustrative of the present invention and that the present invention be limited only by the hereinafter appended claims.

I claim:

1. A method for the preparation of a pharmaceutical composition which consists essentially of:
    (a) mixing as ingredients (1) thymol, (2) camphor, and (3) menthol into (4) *Eucalyptus citriodora* oil;
    (b) heating the mixture to melt the ingredients; and
    (c) cooling the ingredients to provide a colorless oil.

2. The method of claim 1 wherein the treating is by heating the mixture up to about 80° C.

3. The method of claim 1 wherein the treating is by mixing the ingredients over a period of time to provide the colorless mixture.

* * * * *

UNITED STATES PATENT AND TRADEMARK OFFICE
CERTIFICATE OF CORRECTION

PATENT NO. : 7,341,747 B2  Page 1 of 1
APPLICATION NO. : 10/949681
DATED : March 11, 2008
INVENTOR(S) : Muraleedharan G. Nair It is certified that error appears in the above-identified patent and that said Letters Patent is hereby corrected as shown below:

Column 3, line 20, "50 ▫L" should be --50 µL--.

Column 3, line 24, "5▫1/mL" should be --5 µl/mL--.

Signed and Sealed this

Second Day of September, 2008

JON W. DUDAS
*Director of the United States Patent and Trademark Office*